US006987101B1

(12) United States Patent
Nashed

(10) Patent No.: US 6,987,101 B1
(45) Date of Patent: Jan. 17, 2006

(54) THERAPEUTIC GESTAGENS FOR THE TREATMENT OF PREMENSTRUAL DYSPHORIC DISORDER

(75) Inventor: Norman Nashed, München (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/619,493

(22) Filed: Jul. 19, 2000

Related U.S. Application Data

(63) Continuation of application No. 09/331,397, filed as application No. PCT/DE97/03032 on Dec. 22, 1997, now abandoned.

(30) Foreign Application Priority Data

Dec. 20, 1996 (DE) ............................... 196 54 609

(51) Int. Cl.
A61K 31/56 (2006.01)
(52) U.S. Cl. ...................... 514/171; 514/182; 514/170
(58) Field of Classification Search ................ 514/178, 514/182, 173, 171, 170
See application file for complete search history.

(56) References Cited

U.S. PATENT DOCUMENTS 5,583,129 A   12/1996   Spona et al. ................ 514/178

FOREIGN PATENT DOCUMENTS

| DE | 43 13 926 A | 11/1994 |
| DE | 43 44 462 A | 6/1995 |
| EP | 0 640 343 A | 3/1995 |
| WO | 9404157 * | 3/1994 |
| WO | WO 98/27929 A2 * | 7/1998 |

OTHER PUBLICATIONS

Studd et al. (DN 137:273292, CAPLUS, abstract of Advances in Gynecological Endocrinology, Proceedings of the Plenary Sessions of the World Congress of Gynecological Endocrinology, 8th, Florence, Italy, Dec. 6-9, 200 (2002), Meeting Date 2000, 83-89.*
Editors: Genazzani et al.; Parthenon Publishing Group; New York: N. Y.*
Whilbaeck et al. AN 2004:341472 CAPLUS, abstract of Psychoneuroendocrinology (2004), 29(6), 757-766.*
Freeman, E.W, AN 2003:293197, abstract of European J. of Contraceptive & Reproductive Health Care (2002), 7(Suppl. 3), 27 34.*
Toriizuka et al., AN 2000:16283, CAPLUS, abstract of Nippon Yakurigaku Zasshi (2000), 115(1), 21-28.*
Abstract of RAPKIN, Psychoneuroendocrinology Aug. 2003, 28 Suppl 3: 39-53.*
El-Sherbini, Abbas (CA 82:68681, abstract of Ain Shams Med, J. (1974), 25(4), 579-85), 1974.

Boekler, H. (CA 78:24468, abstract of Sportarzt sportmad. (1972), 22(9), 233-4, 236-7, 1972.
Neuman, Friedmund (CA 118:161077, abstract of Pharm. Ztg. (1992), 137(34), 9-15), 1992.
Guenther et al. (CA 113:218253, abstract of WO 9004397), 1974.
Vellacott et al., "A double-blind, placebo-controlled evaluation of spironolactone in the premenstrual syndrome," Current Medical Research and Opinion, vol. 10, No. 7, 1987, pp 450-456.
E. Freeman et al., *Evaluation of a Unique Oral Contraceptive in the Treatment of Premenstrual Dysphoric Disorder*, Journal of Women's Heath & Gender-Based Medicine, vol. 10, No. 6, 2001, pp. 561-569.
E. Freeman et al., *A Double-blind Trial of Oral Progesterone, Alprazolam, and Placebo in Treatment of Severe Premenstrual Syndrome*, JAMA, vol. 274, No. 1, Jul. 5, 1995, pp. 51-57.
P.M. 'Brien et al., *Treatment of Premenstrual Syndrome by Spironolactone*, British Journal of Obstetrics and Gynaecology, vol. 86, Feb. 1979, pp. 142-147.
D. Hellberg et al., *Premenstrual tension: a placebo-controlled efficacy study with spironolactone and medroxyprogesterone acetate*, Int. J. Gynecol. Obstet, 1991; 34: pp. 243-248.
M. Wang et al., *Treatment of premenstrual syndrome by spironolactone: a double-blind, placebo-controlled study*, Acta Obstet Gynecol Scand. 1995: 74:pp. 803-808.
R.B. Bumet et al., *Premenstrual Syndrome and Spironolactone*, Aust NZ J. Obstet Gynaecol 1991; 31: 4: 366.
K. Aslasksen et al., *Spironolactone in the Treatment of Premenstrual Tension: A Double-Blind Study of Spironolactone Versus Bendroflumethiazide and Placebo*, Current Therapeutic Research, vol. 49, No. 1, Jan. 1991, pp. 120-130.
El-Sherbini, Abbas (CA 82:68681, abstract of Aln Shams Med, J. (1974), 25(4), 579-85), 1974.
Boekler, H. (CA 78:24468, abstract of Sportarzi sportmad. (1972), 22(9), 233-4, 236-7, 1972.
Neuman, Friedmund (CA 118:161077, abstract of Pharm. Ztg. (1992), 137(34), 9-15), 1992.
Guenther et al. (CA 113:218253, abstract of WO 9004397), 1974.
L.L. Altshuler et al.: "Pharmacolgical management of premenstrual disorder." Harvard Rev. Psychiat., BD 2 nR. 5, 1995, pp. 233-245.

(Continued)

*Primary Examiner*—Sabiha N. Qazi
(74) *Attorney, Agent, or Firm*—Milen White Zelano & Branigan, P.C.

(57) ABSTRACT

A method for treating premenstrual dysphoric disorder comprises administering a therapeutically effective amount of a gestagen. Optionally, a natural or synthetic estrogen is also administered. In one embodiment, the gestagen and optional estrogen are administered during the luteal phase of the female menstrual cycle, preferably from day 10 to day 28.

21 Claims, No Drawings

OTHER PUBLICATIONS

Christine P. West, "Inhibition of ovulation with oral progestins-effectiveness in premenstrual syndrome," European Journal of Obstetrics & Gynecology and Reproductive Biology. 34 (1990), pp. 119-128.

C. Kirkham, MD., et al., "A Randomized, Double-Blind, Placebo-Controlled, Cross-Over Tral to Assess the Side Effects of Medroxyprogesterone Acetate in Hormone Replacement Therapy," Obstetrics & Gynecology, vol. 78, No. 1, Jul. 1991, pp. 93-97.

L. Dennerstein, et al., "Progesterone and premenstrual syndrome: a double blind crossover trial, "British Medical Journal, vol. 290, Jun. 1, 1985, pp. 1617-1621.

Peter J. Schmidt, MD., et al., "Lack of Effect of Induced Menses on Symptoms in Women with Premenstrual Syndrome," The New England Journal of Medicine, vol. 324, No. 17, Apr. 25, 1991, pp. 1174-1179.

John Bancroft et al., "The Impact of Oral Contraceptives on the Experience of Perimenstrual Mood, Clumsiness, Food Craving and Other Symptoms," Journal of Psychosomatic Research, vol. 37, No. 2, 1993, pp. 195-202.

Cynthia A. Graham, et al., "A Prospective Treatment Study of Premenstrual Symptoms Using a Triphasic Oral Contraceptive," Journal of Psychosomatic Research, vol. 36, No. 3, 1992, pp. 257-268.

Lennart Nilsson et al., "Clinical Studies on Oral Contraceptives-a Randomized, Doubleblind, Crossover Study of 4 Different Preparations (Anovlar® mite, Lyndiol® mite, Ovulen®, and Volidan®)," Acta Obstetrichet Gynecologica Scandinavica, vol. XLVI, Supplement 8, pp. 2-31, yr. 1967.

Johan Cullberg, "Mood Changes and Menstrual Symptoms with Different Gestagen/Estrogen Combinations," Acta Psychiatrica Scandinavica, Supplementum 236, 1972, pp. 9-86.

Sam Silbergeld, Ph.D., MD., et al., "The Menstrual Cycle: A Double-Blind Study of Symptoms, Mood and Behavior, and Biochemical Variables Using Enovid and Placebo," Psychosomatic Medicine, vol. 33, No. 5 (Sep.-Oct. 1971), pp. 411-428.

Francis J. Kane, "Iatrogenic Depression in Women," Phenomenology and Treatment of Depression, Copyright 1977, pp. 69-81.

Mabray et al., "Treatment of Common Gynecologic-Endocrinologic Symptoms by Allergy Management Procedures," Obstetrics & Gynecology, vol. 59, No. 5, May 1982, pp. 560-564.

B.P. Appleby, "A Study of Premenstrual Tension in General Practice," British Medical Journal, Feb. 6, 1960, pp. 391-393.

B. Andersch et al., "Progesterone Treatment of Premenstrual Tension-A Double Blind Study," Journal of Psychosomatic Research, vol. 29, No. 5, 1985, pp. 489-493.

Michael A. Richter, M.D., et al., "Progesterone Treatment of Premenstrual Syndrome," Current Therapeutic Research, vol. 36, No. 5, Nov. 1984, pp. 840-850.

Gwyneth A Sampson, "Premenstrual Syndrome: A Double-Blind Controlled Trial of Progesterone and Placebo," Brit. J. Psychiat. (1979), 135, 209-215.

Sarah Maddocks, et al., "A double-blind placebo-controlled trial of progesterone vaginal suppositories in the treatment of premenstrual syndrome," Am J Obstet Gynecol, Mar. 1986, pp. 573-581.

Ellen Freeman, et al., "Ineffectiveness of Progesterone Suppository Treatment for Premenstrual Syndrome," JAMA, vol. 264, No. 3, Jul. 18, 1990, pp. 349-353.

Lorraine Dennerstein, et al., "Treatment of Premenstrual Syndrome a Double-blind Trial of Dydrogesterone," Journal of Affective Disorders, 11 (1986), pp-199-205.

Gwyneth A. Sampson, et al., "Premenstrual Syndrome A Double-blind Cross-over study of Treatment with Dydrogesterone and Placebo," British Journal of Psychiatry, 153 (1988), pp. 232-235.

Pekka Ylostalo, et al., "Bromocriptine and Norethisterone in the Treatment of Premenstrual Syndrome," Obstetrics & Gynecology, vol. 58, No. 3, Mar., 1982, pp. 292-298.

Malinee Sangthawan et al., A comparative study of monophasic oral contraceptives containing either drospirenone 3 mg or levonorgestrel 150 $\mu$g on premenstrual symptoms, Science Direct, Jul. 19, 2004.

* cited by examiner

THERAPEUTIC GESTAGENS FOR THE TREATMENT OF PREMENSTRUAL DYSPHORIC DISORDER

This is a continuation of application Ser. No. 09/331,397 filed Jun. 21, 1999, now abandoned, which is a 371 of PCT/DE97/03032, filed Dec. 22, 1997. Priority of application No. 196 54 609.5 filed on Dec. 20, 1996 in Germany is claimed under 35 U.S.C. §119.

This invention relates to the use of therapeutic gestagens for the treatment of premenstrual dysphoric disorder (PMDD).

An accurate diagnosis and an effective treatment are essential to treat or to mitigate this disorder. The diagnosis is confirmed only in about 25% of women who report PMDD, when the symptoms are observed over another cycle. The most important symptoms are a state of emotional stress, irritability, unease and the feeling of being out of control. The first occurrence of PMDD is usually in one's late 20s, although it doesn't usually occur in patients until their mid-30s.

PMDD manifests itself by the occurrence of at least 5 of the 11 symptoms that are listed below; the latter must occur to a serious extent premenstrually and lessen postmenstrually. These 5 symptoms must comprise at least one dysphoric symptom (irritability, mood swings, anxiety conditions or depression). Several physical symptoms are counted as one symptom.

Criteria for the Existence of Premenstrual Dysphoric Disorder

In the prospective evaluation by recording the symptoms of the patient over 2 or 3 menstrual cycles, 5 (or more) of the symptoms that are listed below occur during the last week of the luteal phase, but no longer occur postmenstrually. At least one of the symptoms must be the first, second, third or fourth symptom below.

1. Noticeably stressed mental state, feelings of hopelessness or self-doubt
2. Noticeable feeling of anxiety, tension, feeling of "being on the edge"
3. Noticeable emotional tendencies (e.g., suddenly feeling sad or fretful or increased sensitivity to rejection)
4. Lasting and noticeable feelings of unease or irritability or increased interpersonal conflicts
5. Decreasing interest in conventional activities (e.g., work, school, friends, hobbies)
6. Subjective sensation of concentration difficulties
7. Lethargy, slight exhaustion or noticeable lack of energy
8. Noticeable change in appetite, overeating or special food cravings
9. Hypersomnia or insomnia
10. Subjective feeling of being overwhelmed or out of control
11. Other physical symptoms, such as breast tenseness or swelling, headaches, joint or muscle pains, floating sensation, weight gain.

The listed disorders must have noticeably adverse effects wtih respect to work or school or conventional social activities and relationships to others. The disorders must not be an aggravation of the symptoms of other disorders (e.g., greater depressive disorder, panic disorder, dysthymic disorder, personality disorder).

Otherwise, reference is also made to the DSM-IV, American Psychiatric Association: Diagnostic and Statistical Manual of Mental Disorders, 4th Edition, Washington, D.C., America Psychiatric Association, 1994, p. 715 ff, "Premenstrual Dysphoric Disorder."

Since the symptoms of PMDD seem to be associated with the progesterone cycle, the hope was that hormonal therapies could be helpful to the treatment of PMDD. This hope has not been confirmed. Hormone therapies lead only to mixed results. Hormone antagonists are more likely indicated for the treatment of somatic symptoms of the premenstrual symptom (PMS) than PMDD.

To date, selective serotonin reuptake inhibitors (SSRIs; e.g., fluoxetines, sertralines) and other psychotropic active ingredients (e.g., alprazolam) are considered as most effective for symptomatic treatment of PMDD.

A treatment with these compounds can cause serious side effects; in addition, only a portion of the symptoms that constitute the PMDD image of disease can be mitigated with psychotropic active ingredients.

The object of this invention is to indicate an effective pharmaceutical agent for the treatment of PMDD, which avoids the drawbacks of pharmaceutical agents used to date.

It has been found that therapeutic gestagens can be used for the production of medications for the treatment of PMDD. This is very surprising, since hormonal treatments had already been considered but had not turned out to be helpful.

Therapeutic gestagens are defined as those gestagens that in addition to their gestagenic action have a partial profile that is advantageous for therapeutic purposes, i.e., that additionally exert an antiandrogenic action and optionally also an anti-mineral-corticoidal action. This additional action must occur as early as at a dosage at which a gestagenic effect also occurs.

Examples of such therapeutic gestagens that are to be used according to the invention are cyproterone acetate, dienogest and especially drospirenone. While the first two exhibit gestagenic and antiandrogenic action, drospirenone, like the natural progesterone, has an additional anti-mineral-corticoidal action. In contrast to the natural hormone, it is also bioavailable after oral administration.

The exact history of the origin of PMDD is unknown to date. Both the fluctuation of ovarian steroid hormones and the water retention in the luteal phase of the menstrual cycle demonstrably play a role in PMDD. In this case, it appears to provide interaction between the ovarian steroid hormones and neutrotransmitters, such as, e.g., serotonin.

The symptoms of PMDD are mitigated by the antiandrogenic action of therapeutic gestagens. Increased testosterone levels during the late luteal phase were used to explain the irritative and impulsive form of phenomena that characterize the premenstrual state of PMDD that readily responds to irritants. Testosterone levels, especially in the case of free testosterone, have a positive correlation with premenstrual irritability (Eriksson, E. et al., Serum Levels of Androgens Are Higher in Women with Premenstrual Irritability and Dysphoria than in Controls, Psychoneuroendocrinology 1992: 17, 195–204).

In addition, improvement of the general mental state (general mood symptoms) is achieved by treatment with a therapeutic gestagen. This must be all the more surprising than only psychotropic active ingredients having been used to date for treatment. This improvement is documented in a "Quality of Life" study.

Based on the anti-mineral-corticoidal properties of the gestagen drospirenone, a reduction of the physical symptoms, such as breast tenseness or swelling, headaches, floating sensation, or weight gain, start with a feeling of tightness through the clothing, shoes or rings.

A pharmaceutical agent according to the invention can contain either a therapeutic gestagen by itself or a therapeutic gestagen in combination with an estrogen. Both natural and synthetic estrogens are suitable as estrogens.

The dosage of the therapeutic gestagens is to be 0.5 mg to less than 5 mg, preferably 1.0 to 4.0 mg per day in the case of drospirenone or an equivalent-action amount of another therapeutic gestagen.

The gestagenic and estrogenic active ingredient components are preferably administered orally together. The daily dose is preferably administered one time.

As estrogens, all natural and synthetic compounds that are known as being estrogenically active are suitable.

As natural estrogens, these are especially estradiol and also its longer-acting esters, such as valerate, etc., or estriol.

Synthetic estrogens, such as ethinylestradiol, $14\alpha,17\alpha$-ethano-1,3,5(10)-estratriene-3,17$\beta$-diol (WO 88/01275), $14\alpha,17\alpha$-ethano-1,3,5(10)-estratriene-3,16$\alpha$,17$\beta$-triol (WO 91/08219) or the 15,15-dialkyl derivatives of estradiol, and of these especially 15,15-dimethylestradiol, can preferably be mentioned. As a synthetic estrogen, ethinylestradiol is preferred.

Also, the estratrien-3-amidosulfonates (WO 96/05216 and WO 96/05217) that are derived from estradiol or ethinylestradiol, that are distinguished by low hepatic estrogeneity and that have become known recently are suitable as estrogens for common use with the compounds of general formula I.

Finally, the 14a,15a-methylene steroids from the estrane series, especially the 14,15a-methylen-17a-estradiol and the corresponding 3-amidosulfonate derivatives can be mentioned.

The estrogen is administered in an amount that corresponds to that of 0.010 to 0.05 mg of ethinylestradiol or 1.0 to 3.0 mg daily.

The formulation of the pharmaceutical preparations based on the new compounds is carried out in a way that is known in the art, by the active ingredient, the therapeutic gestagen, optionally in combination with an estrogen, being processed with the vehicles, diluents, optionally taste correctives, etc., that are commonly used in galenicals and being converted into the desired form of administration.

For the preferred oral administration, especially tablets, coated tablets, capsules, pills, suspensions or solutions are suitable.

For parenteral administration, especially oily solutions, such as, for example, solutions in sesame oil, castor oil and cottonseed oil, are suitable. To increase solubility, solubilizers, such as, for example, benzyl benzoate or benzyl alcohol, can be added.

The therapeutic gestagen, optionally in combination with an estrogen, can also be administered continuously by an intrauterine release system (IUD); in this case, the release rate of the active compound(s) is selected in such a way that the dose that is released daily lies within the already indicated dosage range.

In the case of a mono-preparation that contains only one therapeutic gestagen, the latter can be created for the administration of daily dosage units over the entire menstrual cycle.

According to a variant of the invention, the pharmaceutical agent for treatment of PMDD is administered only during the luteal phase of the cycle, beginning at the earliest on day 10 until the end of the cycle, usually up to day 28. An extended administration is also conceivable.

If the therapeutic gestagen according to this invention is used in combination preparations together with an estrogen, these preparations can be provided for continuous, sequential or cyclic administration of active ingredients.

Continuous administration is defined here as the daily common administration of the two active ingredients.

Sequential administration means administration of the therapeutic gestagen starting on day 10 at the earliest until the end of the cycle. Administration from day 10 to 28 is preferably meant here. Together with the gestagen, the estrogen is administered, separately or in the same dosage unit. In addition, the estrogen is administered on a few or all of the gestagen-free days.

Cyclic administration is defined as the administration of the two active ingredients starting from the first day of the cycle until a time before the last day of the cycle, preferably day 21 to day 23.

Based on the ovulation-inhibiting properties of the therapeutic gestagen or the combination preparations of gestagen and estrogen, these preparations are also suitable for contraception, if the active components are contained in amounts that are adequate for this purpose. These preparations are therefore preferably used for symptomatic treatment of women of child-bearing age with average to serious symptoms of PMDD. In this case, the use of the therapeutic gestagen is preferably carried out with a synthetic estrogen, such as ethinylestradiol.

Combination preparations of a therapeutic gestagen with a natural estrogen, especially estradiol, can be used preferably for symptomatic treatment of average to serious symptoms of PMDD in perimenopausal women. Perimenopause begins with the occurrence of menopausal symptoms and ends one year after menopause, the last menstruation.

In especially serious cases of PMDD, the pharmaceutical agent according to the invention can also be used in connection with a psychotropic medication of the above-mentioned type.

The example below is used for a more detailed explanation of the invention:

Fertile women, who were classified according to the above-indicated criteria 1. to 11. as PMDD patients, are treated orally over at least 4 cycles, in each case from day 1 to day 21 of the cycle daily, with an amount of 3 mg of drospirenone together with 30 $\mu$g of ethinylestradiol. Then come 7 pill-free days or 7 daily placebos. After a treatment over 4 to 6 cycles, the symptoms that fall into the category criteria 1. to 11. are carefully evaluated again. In the case of all of the women treated, a significant improvement relative to at least one of the symptoms that occurred before the beginning of the treatment, but not only the 11th symptom, is observed.

I claim:

1. A method of treating premenstrual dysphoric disorder, comprising administering to a patient in need of such treatment a therapeutically effective amount of a gestagen, which is drospirenone.

2. A method of treating premenstrual dysphoric disorder comprising administering to a patient in need of such treatment a therapeutically effective amount of a gestagen, which is drospirenone, further comprising an estrogen.

3. The method of claim 2, wherein the estrogen is synthetic.

4. The method of claim 3, wherein the estrogen is ethinylestradiol.

5. The method of claim 2, wherein the estrogen is an estrogen sulfamate.

6. The method of claim 2, wherein the estrogen is natural.

7. The method of claim 6, wherein the estrogen is estradiol, estradiol valerate or another estradiol ester.

8. The method of claim 1, wherein the gestagen is administered only during the luteal phase of the female menstrual cycle.

9. The method of claim 8, wherein the gestagen is administered from day 10 to 28 of the menstrual cycle.

10. The method of claim 1, wherein the gestagen administered in an amount of 0.5 mg to less than 5 mg daily.

11. The method of claim 4, wherein the ethinylestradiol is administered in an amount of 0.010 to 0.05 mg daily.

12. The method of claim 7, wherein estradiol is administered in an amount of 1.0 to 3.0 mg daily.

13. The method of claim 3, wherein the gestagen and estrogen are administered together.

14. The method of claim 13, wherein the gestagen and estrogen are administered orally.

15. The method of claim 7, wherein the estrogen is estradiol.

16. The method of claim 10, wherein the daily dose of drospirenone is 1.0 to 4.0 mg.

17. The method of claim 3, wherein the estrogen is an estratrien-3-amidosulfonate.

18. The method of claim 3, wherein the estrogen is a 14a,15a-methylene steriod from the estrane series.

19. The method of claim 2, wherein the gestagen and estrogen are administered continuously.

20. The method of claim 2, wherein the gestagen and estrogen are administered sequentially.

21. The method of claim 2, wherein the gestagen and estrogen are administered cyclically.

* * * * *

UNITED STATES PATENT AND TRADEMARK OFFICE
CERTIFICATE OF CORRECTION

PATENT NO.         : 6,987,101 B1
APPLICATION NO.    : 09/619493
DATED              : January 17, 2006
INVENTOR(S)        : Norman Nashed It is certified that error appears in the above-identified patent and that said Letters Patent is hereby corrected as shown below:

Column 5, line 8-9, reads "gestagen administered" should read -- gestagen is administered --
Column 5, line 14, reads "method of claim 3" should -- method of claim 2 --
Column 6, line 8, reads "steriod" should read -- steroid --

Signed and Sealed this

Fifteenth Day of August, 2006

JON W. DUDAS
*Director of the United States Patent and Trademark Office*